United States Patent [19]
Thorne et al.

[11] Patent Number: 5,776,157
[45] Date of Patent: Jul. 7, 1998

[54] LANCET APPARATUS AND METHODS

[75] Inventors: Gale H. Thorne; Gale H. Thorne, Jr., both of Bountiful; Charles V. Owen, Highland; Gary H. Stout, Farmington; Tim L. Farnes, North Salt Lake, all of Utah

[73] Assignee: Specialized Health Products, Inc., Bountiful, Utah

[21] Appl. No.: 720,699

[22] Filed: Oct. 2, 1996

[51] Int. Cl.$^6$ .................................. A61B 17/32
[52] U.S. Cl. ........................................... 606/182
[58] Field of Search ..................... 606/181, 182, 606/183; 128/760, 762, 771; 204/206; 206/569–571

[56] References Cited

U.S. PATENT DOCUMENTS

| | | | |
|---|---|---|---|
| 4,627,445 | 12/1986 | Garcia | 128/770 |
| 4,637,403 | 1/1987 | Garcia | 128/770 |
| 4,715,374 | 12/1987 | Maggio | 606/181 |
| 4,735,203 | 4/1988 | Ryder et al. | 606/181 |
| 4,995,402 | 2/1991 | Smith | 128/771 |
| 5,047,044 | 9/1991 | Smith | 606/182 |
| 5,152,775 | 10/1992 | Ruppert | 606/181 |
| 5,514,152 | 5/1996 | Smith | 606/182 |

FOREIGN PATENT DOCUMENTS 20365196  10/1989  European Pat. Off. ......... A61B 5/14

OTHER PUBLICATIONS

EP–365–196–A.
Tenderlett Package Insert, International Technidyne Corp., 23 Nevsky Street, Edison, N.J. 08820, no publication date.
Unistik Product Brochure, Ulster Scientific, Inc., P.O. Box 819, New Paltz, NY 12561–0819, no publication date.
Sureject Product Brochure, Gainor Medical U.S.A. Inc., P.O. Box 92077, Long Beach, CA 90809–2077, no publication date.
Surelet Product Brochure, Gainor Medical U.S.A. Inc., P.O. Box 92077, Long Beach, CA 90809–2077, no publication date.
Ultra TLC Lancet Product Brochure, MediSense Inc., 128 Sidney Street, Cambridge, MA 02139, no publication date.
Insul–eze Product Brochure, Palo Laboratoties, 1595 Soquel Dr., Santa Cruz, CA 95065, no publication date.
Turner & R.R. Holman, "Automatic Lancet for Capillary Blood Sampling", *The Lancet*, Sep. 30, 1978, p. 712.

*Primary Examiner*—Michael Buiz
*Assistant Examiner*—Nancy Mulcare
*Attorney, Agent, or Firm*—Gale H. Thorne

[57] ABSTRACT

A one-time-use, self-powered, disposable lancet apparatus packaged both as strips comprising a plurality of lancets and as individually packaged lancets. A novel lancet blade design comprises means for attaching each blade in a loader stack for an automated assembly machine. Individually packaged lancets are disclosed in both one-step and two-step embodiments. In each case, every lancet comprises a self-contained package which houses a powered lancet blade before use and a spent blade after use to assure safety from inadvertent sticks both before and after a lancing procedure.

15 Claims, 15 Drawing Sheets

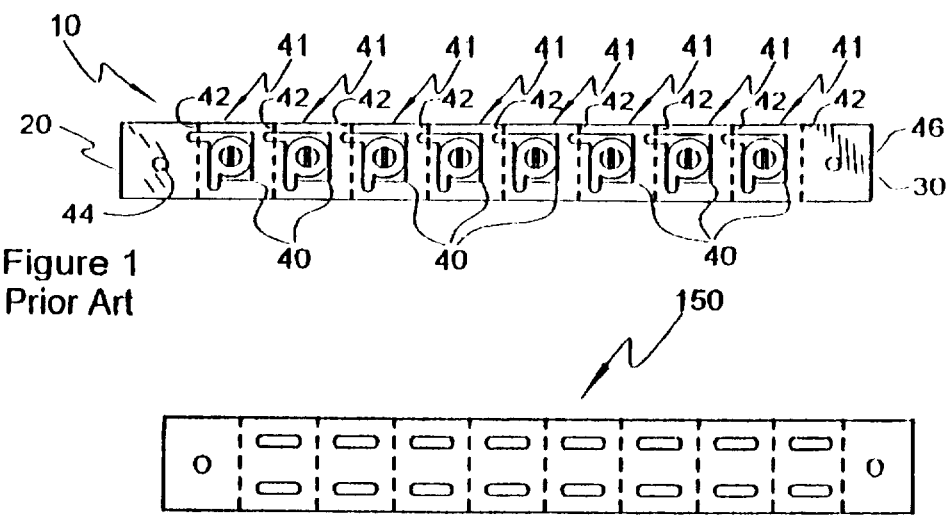
Figure 1
Prior Art
Figure 3
Prior Art
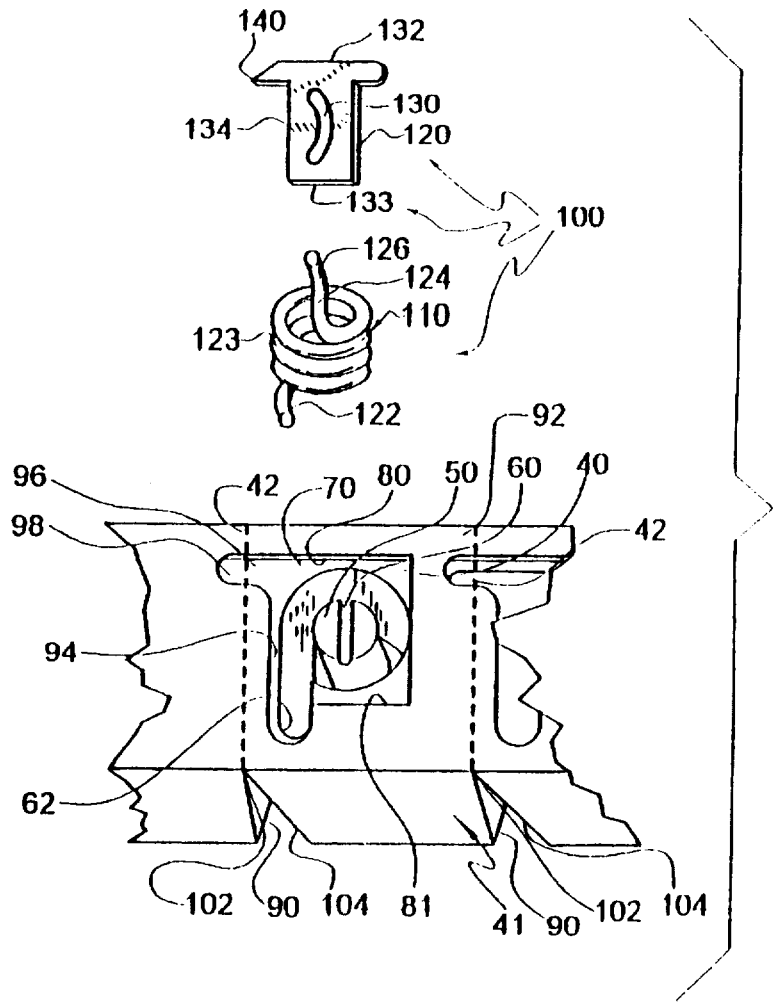
Figure 2
Prior Art

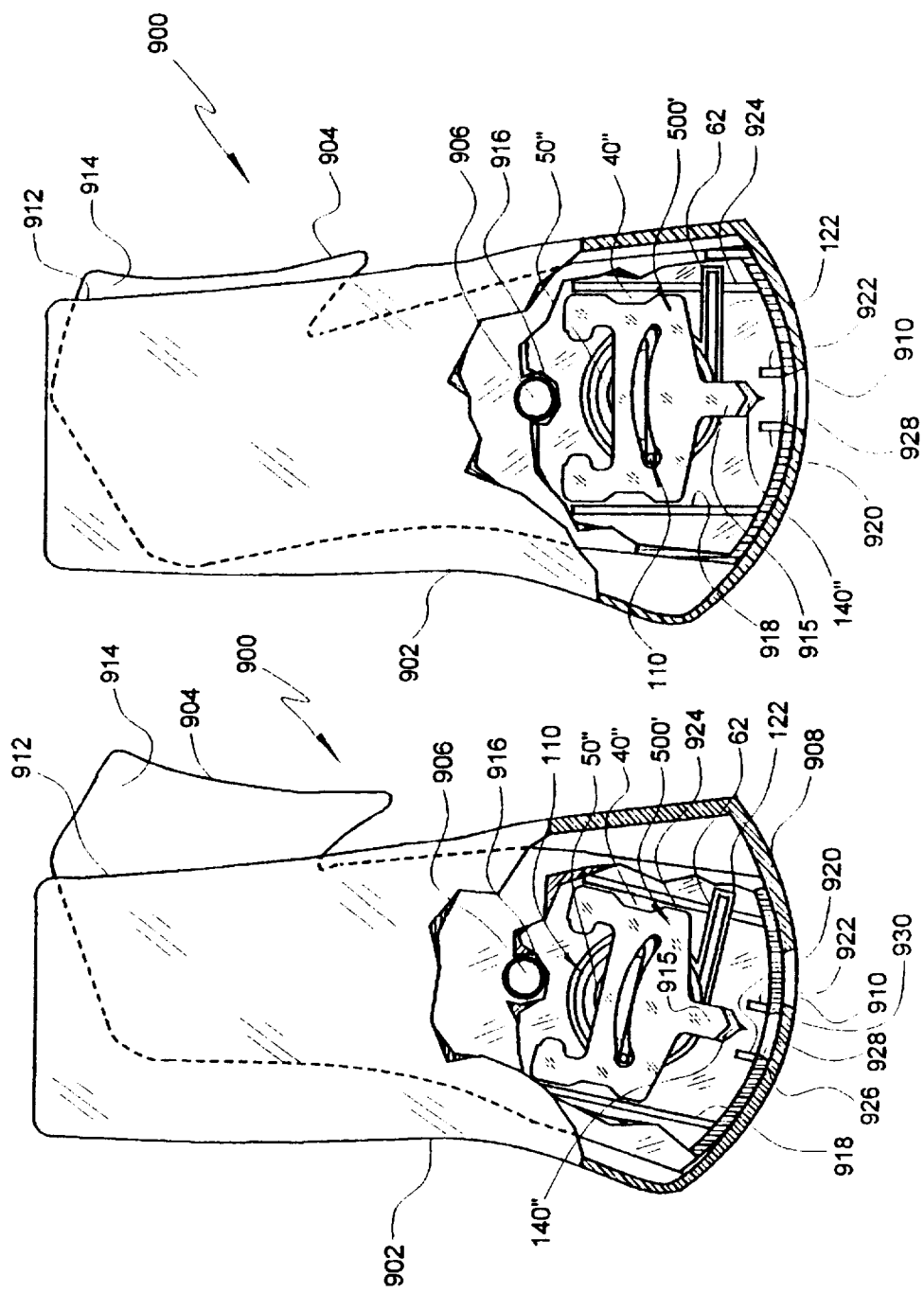

LANCET APPARATUS AND METHODS

BACKGROUND OF THE INVENTION

1. Field of the Invention

This invention relates generally to lancets and more particularly to novel, self-contained, precocked and single-use lancets which, when activated, extend a tip of a lancet blade outward from a lancet housing and back into the housing for safe disposal. In a preferred embodiment, the housing is sealed to maintain sterility of the blade before use. A portion of the housing is preferably frangible, and the portion is franged to initiate a single lancing cycle and to subsequently make the lancet unreusable.

2. Related Art

In particular, U.S. Pat. No. 5,514,152 (Smith), issued May 7, 1996, discloses a lancet having a cocked torsion spring wound about a centrally disposed hub frangibly connected to a lancet housing. Generally, the housing is disclosed to be a container for a plurality of lancets, each of which, after use, is frangibly separated from the rest of the strip and individually discarded. The spring is directly interconnected to a lancet blade in a cam/cam follower relationship. When the hub is frangibly separated from the housing, the cocked spring is released to drive a lancet blade tip linearly from the housing and then return it safely back into the housing.

Smith discloses frangible separation of the hub from the housing where a base of the hub is annularly connected by sharp corners to the housing. It is taught that stress placed upon the base causes the hub to frange from the housing, permitting the lancing cycle to begin. Of course, before each lancing cycle is initiated, a housing exit is exposed to provide an orifice through which the lancet blade tip travels. It is only when the orifice is provided that the sterility of the package is compromised making the blade and internal contents sterile until that time.

BRIEF SUMMARY AND OBJECTS OF THE INVENTION

In brief summary, this novel invention alleviates all known major problems related to providing a molded housing for both a lancet strip and single lancet device and further combines a lancet carrier with a lancet housing into a unitary single lancet device. One and two activation step embodiments of the single lancet devices are disclosed, the one step embodiments being presently preferred. Generally, the one step embodiments comprise a single action (step) by a user, but two functions (breaking of a sterile barrier and initiation of a lancet cycle) are combined in the single step. Commonly, the two step embodiments require a first step to break a sterile barrier and a second step to initiate a lancet cycle. While there are few other advantages or disadvantages to one or two step operation, the first step of the two step embodiment is often regarded as causing lost or wasted time by a user.

Similar to Smith (cited above), the invention comprises a rapidly outwardly driven and then inwardly retracted lancet blade in a cycle which is initiated by franging a hub, disposed within and securely affixed to a cocked spring, from an integrally associated housing. This invention, however, embodies a novel molded interconnection between hub and housing to assure that the hub will be easily franged from the housing and will rotate freely within the spring and not comprise extraneous fragments about edges at frange sites which can catch upon other edges of the housing and inadvertently keep the spring from unwinding and therefore the blade from completing a lancing cycle.

Accordingly, it is a primary object of the present invention to provide a one-time-use, self-driven lancet having a readily frangible, molded connection between a hub and housing which permits the hub to separate from the housing without extraneous fragments being disposed about the hub where the hub/housing frange is disposed.

It is another primary object to provide a single, one-time-use lancet embodiment in which a carrier and lancet housing are combined in a single disposable unit.

It is an important object to provide an embodiment of the single, one-time-use lancet which operates in two steps, one of which is to break a sterile barrier and the other of which is to initiate a lancet cycle.

It is an object of premier importance to provide an embodiment of the single, one time use lancet which operates in a single step, wherein the breaking of a sterile barrier and initiating of a lancet cycle are performed in a single operating step.

It is an object to provide an embodiment of the single, one-time-use lancet which operates in the single step of squeezing two displaced, but juxtaposed parts together to perform the two steps of breaking the sterile barrier and initiating the lancet cycle.

It is an important object to provide a lancet blade which is facilely used in automated assembly of a lancet.

It is also an important object to provide a strip of presterilized lancets from which a used lancet is frangibly separated without disturbing the sterile condition of any other lancet in the strip.

It is a very important object to provide a lancet housing having a molded hub which is freely frangibly separated from the rest of the housing.

These and other objects and features of the present invention will be apparent from the detailed description taken with reference to accompanying drawings.

BRIEF DESCRIPTION OF THE DRAWINGS

FIG. 1 is a planar view showing the inner surface of a prior art representation of a lancet housing assembly member;

FIG. 2 is an exploded perspective view of a lancet housing assembly compartment of the lancet housing assembly member showing in FIG. 1 comprising a lancet blade and torsion spring in cocked orientation;

FIG. 3 is a planar view of the inner surface of a prior art representation of a cover for the lancet housing assembly member;

3

Figure 9:
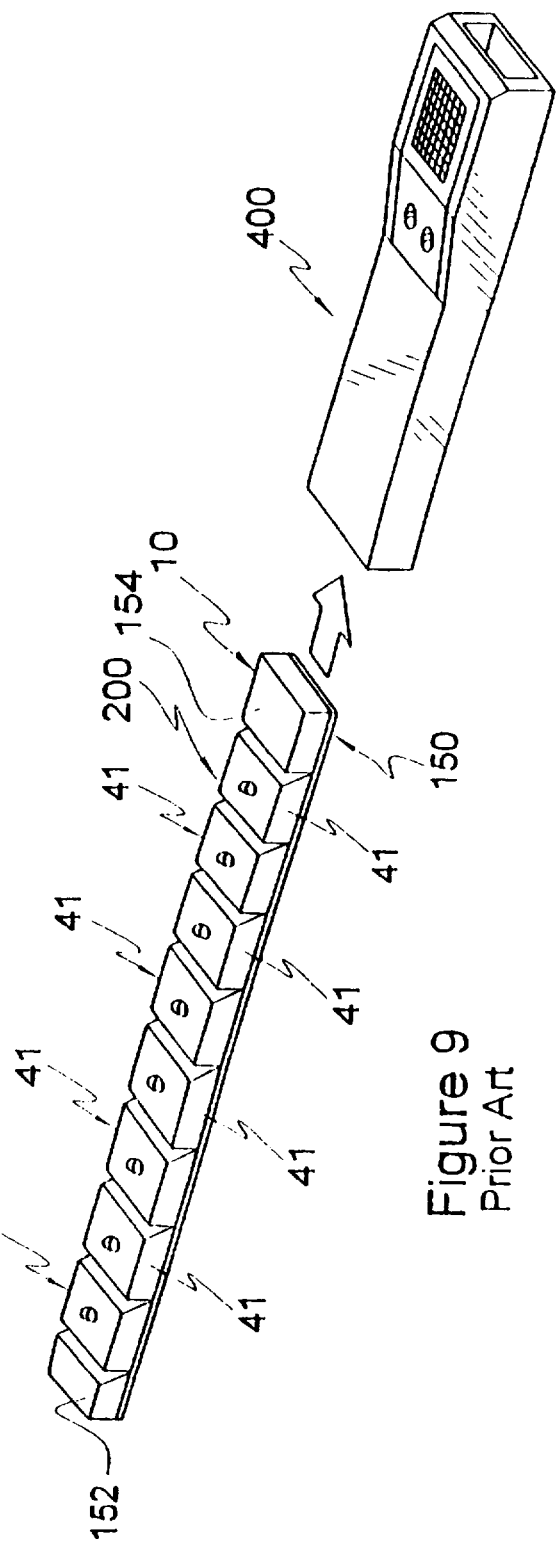
FIG. 9 is a perspective drawing showing a prior art representation of direction of insertion of a lancet housing into a housing carrier.
Figure 10:
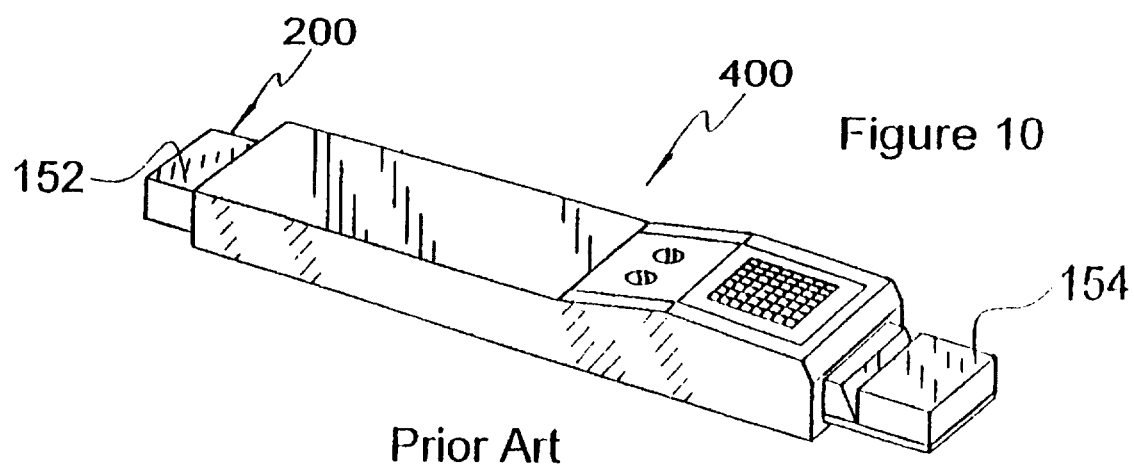
Figure 11:
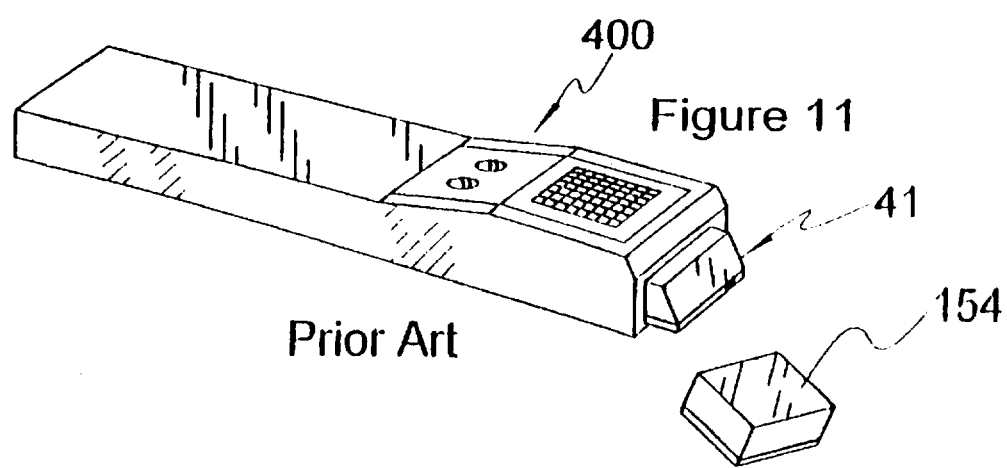
Figure 12:
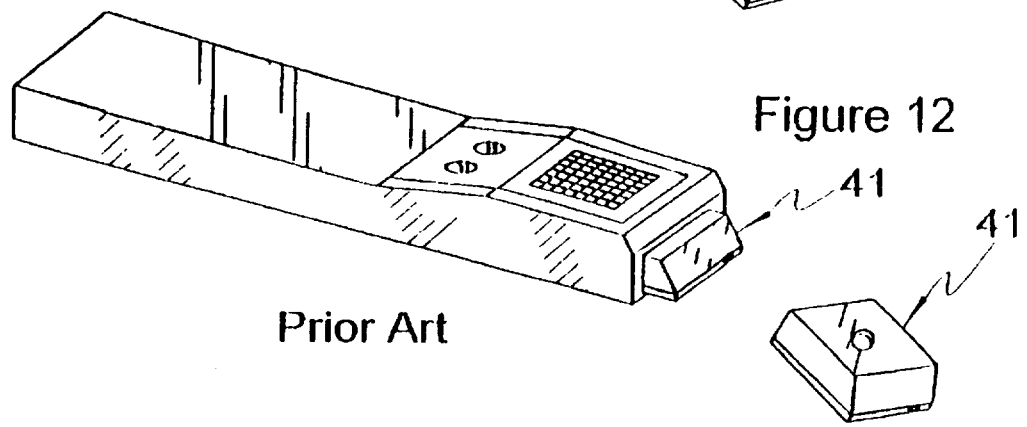
Figure 13:
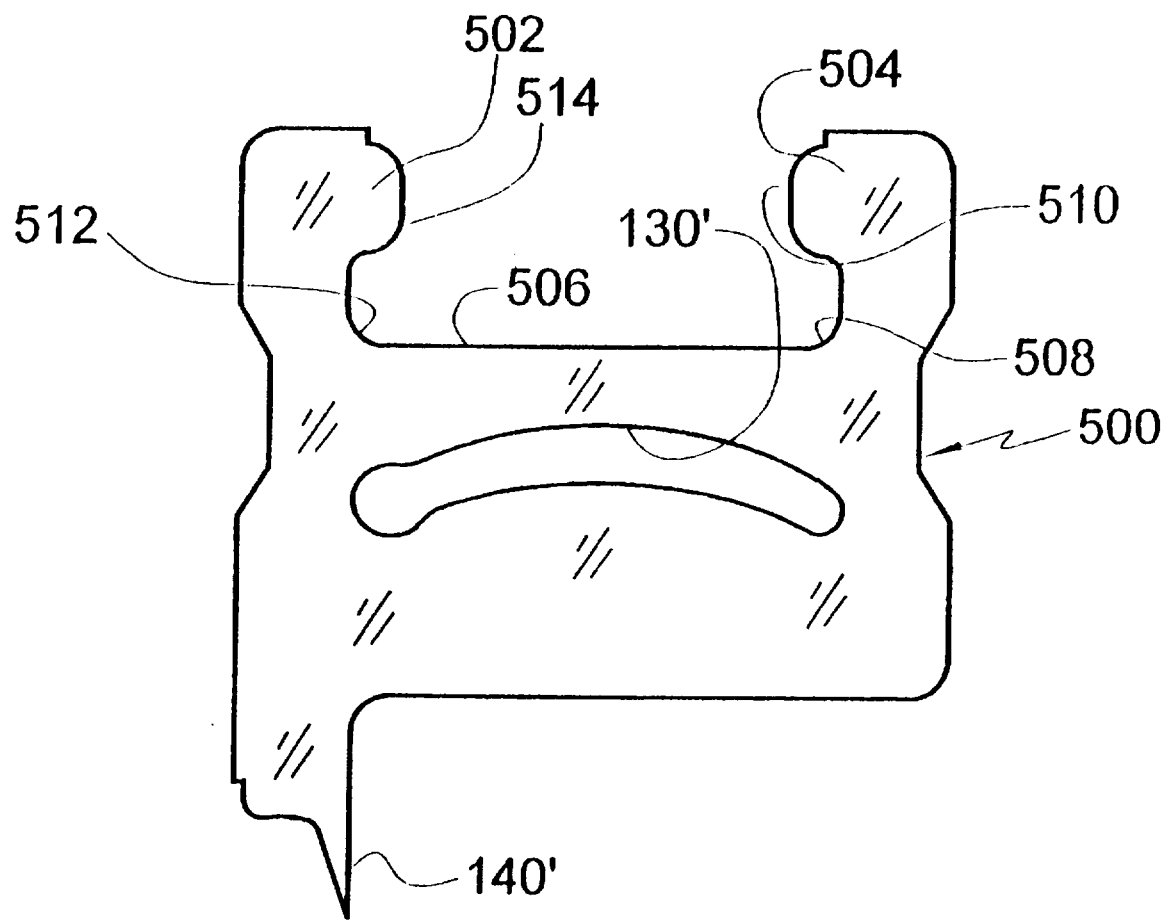
Figure 14:
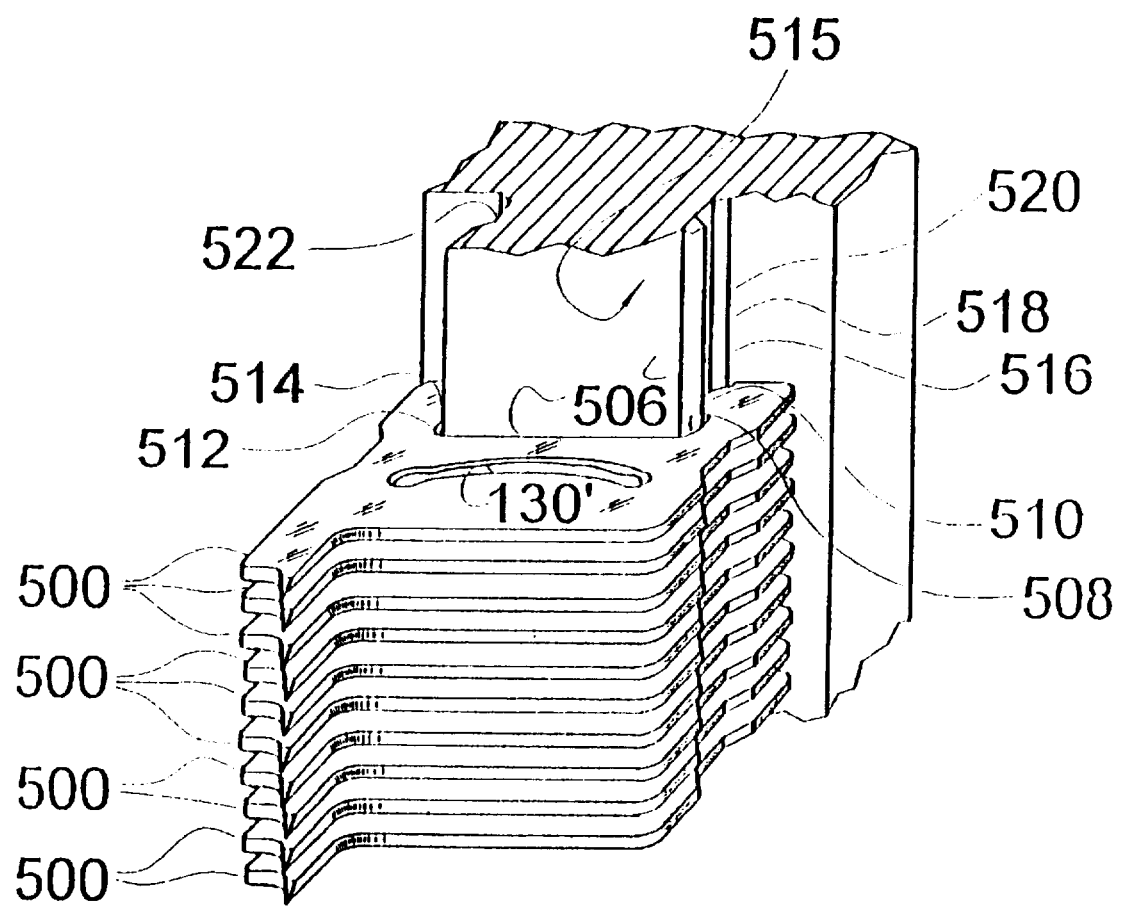
Figure 15:
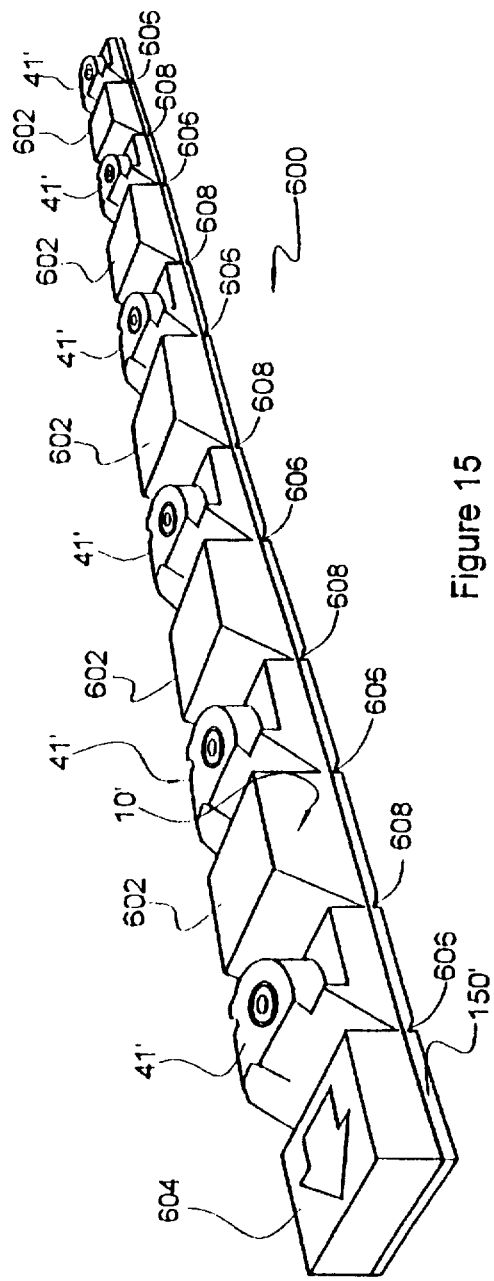
Figure 16:
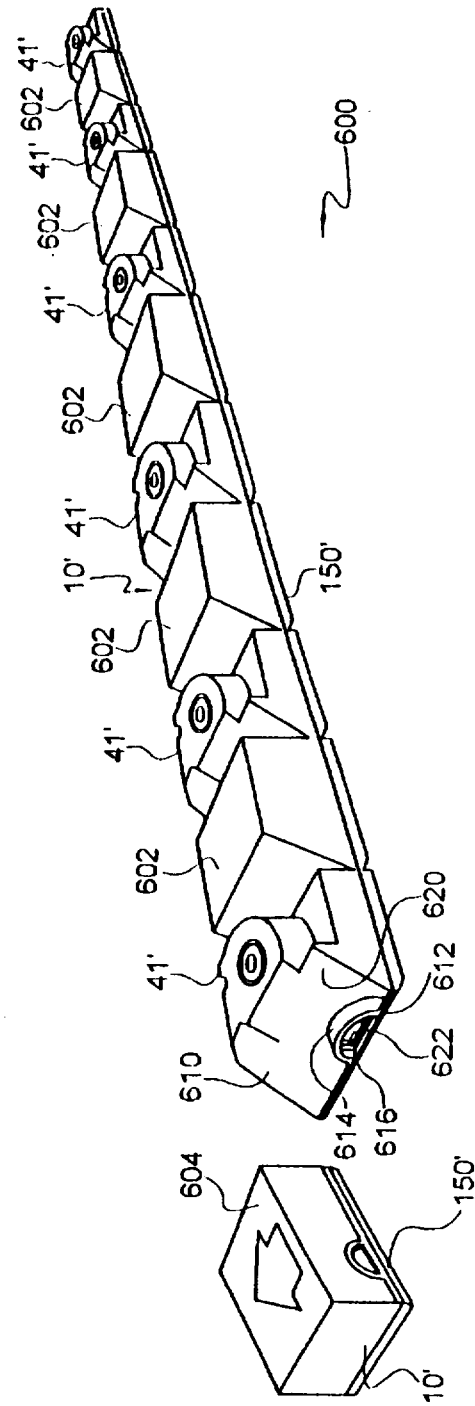
Figure 17:
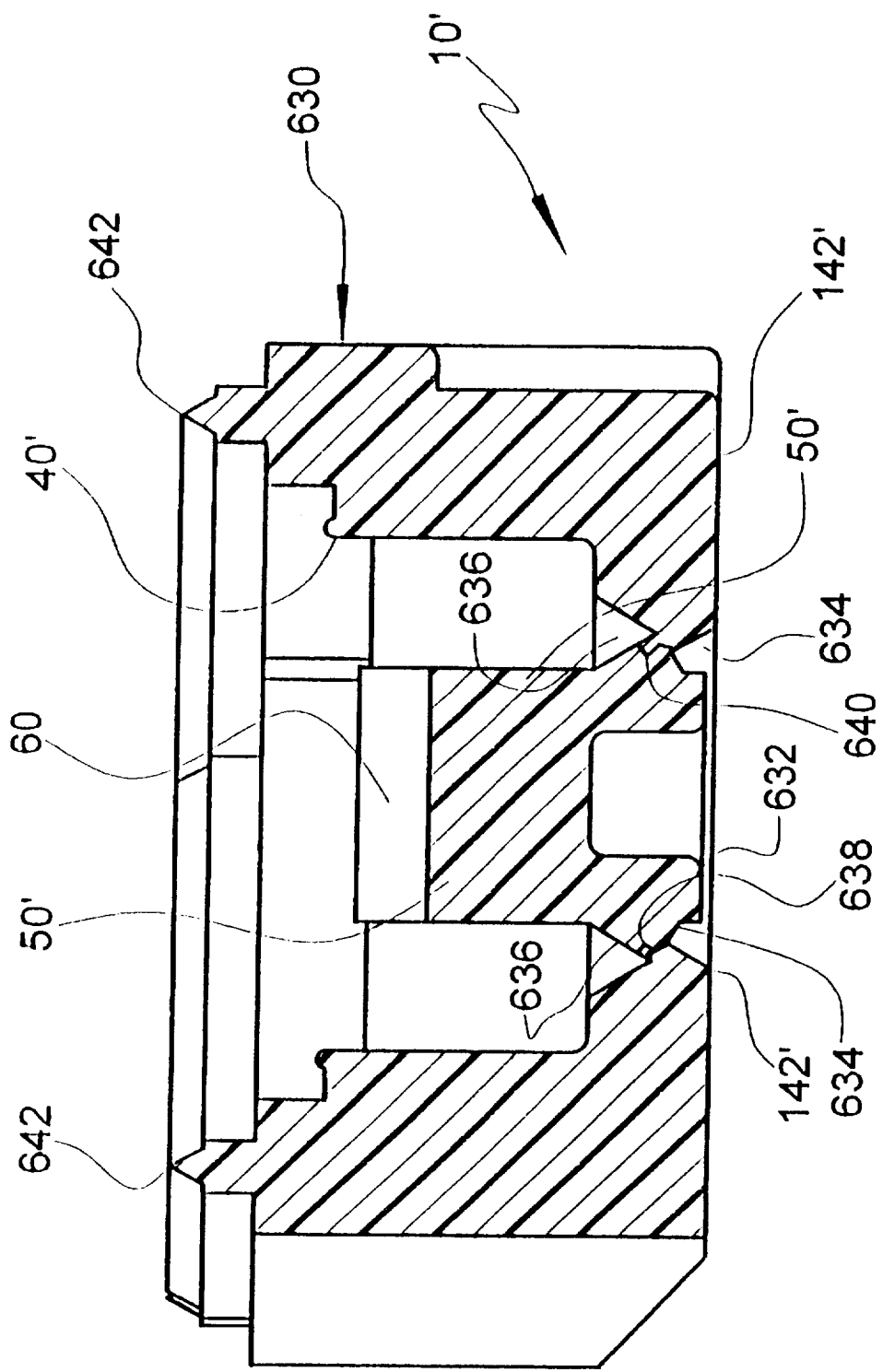
Figure 18:
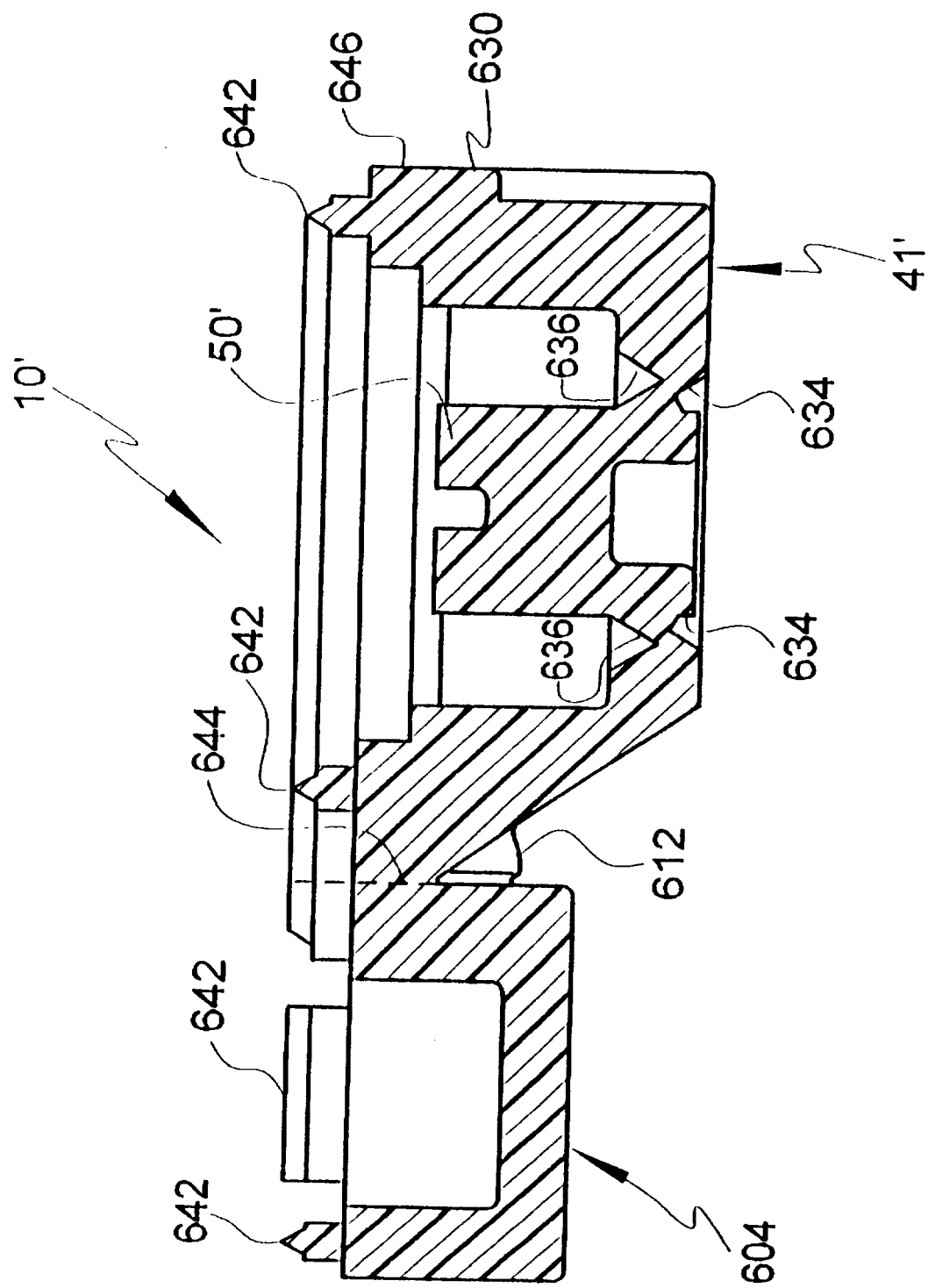
Figure 20:
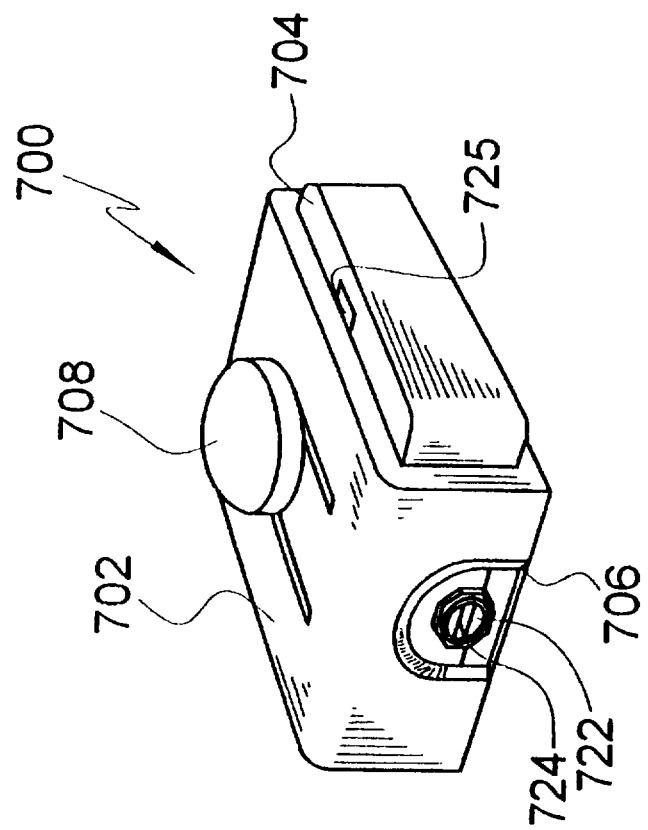
Figure 19:
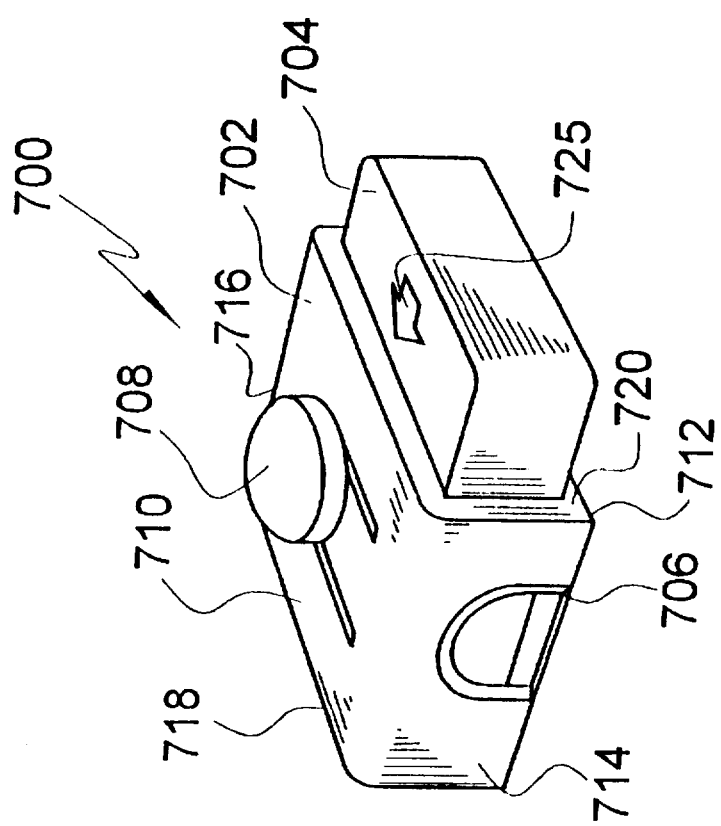
Figure 22:
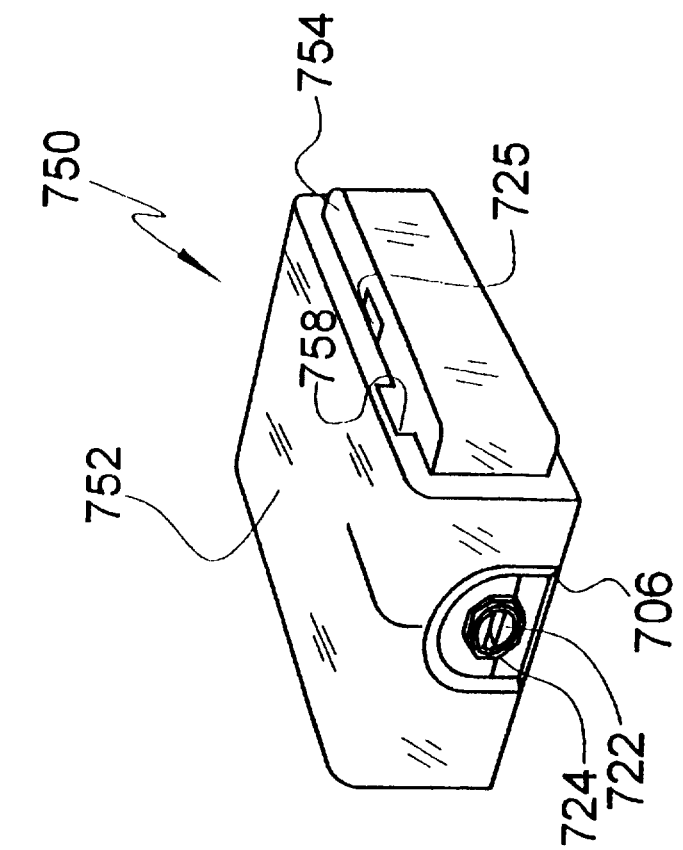
Figure 21:
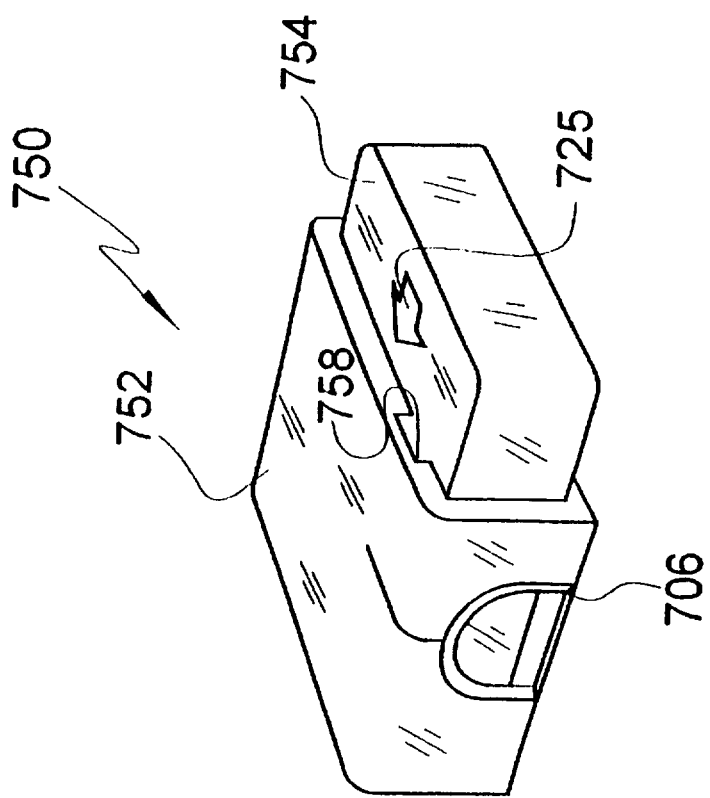
Figure 23:
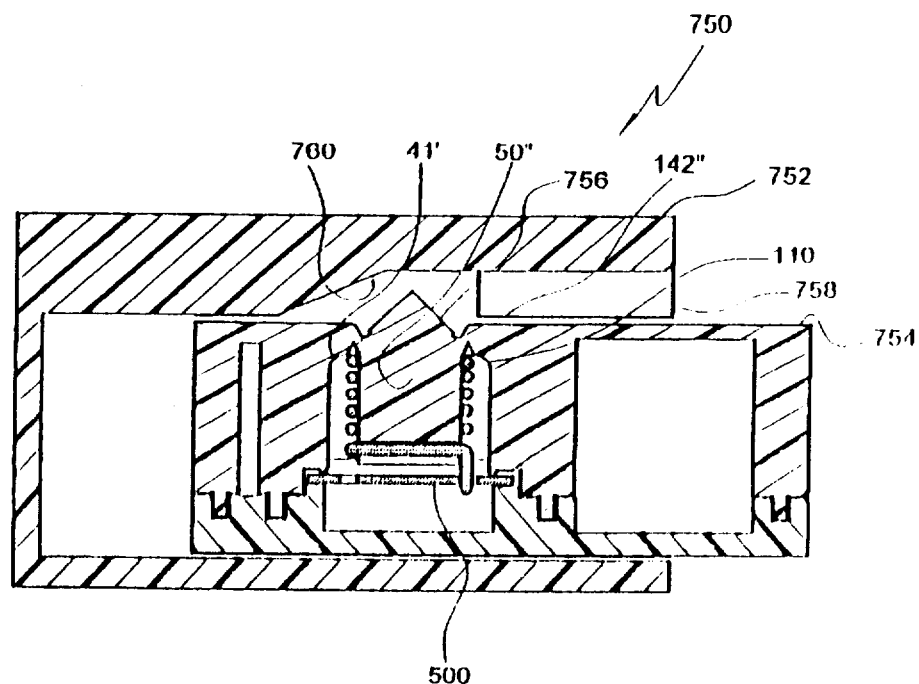

FIG. 10 is a perspective drawing showing initial position of the lancet housing, seen in FIG. 9, properly inserted into the housing carrier;

FIG. 11 is a perspective drawing of the housing and carrier of FIG. 10 showing the distal end of a lancet compartment newly exposed by frangible separation from a preceding compartment revealing an exit aperture for a first to-be-used lancet;

FIG. 12 is a perspective drawing of the housing and carrier of FIG. 11 showing a used lancet compartment frangibly separated from the remainder of the housing revealing an exit aperture for a next to-be-used lancet;

FIG. 13 is a top elevation view of a lancet blade of the present invention;

FIG. 14 is a perspective of a plurality of blades affixed to a blade magazine used to automatically load blades into lancet housings;

FIG. 15 is a perspective of a strip of lancets comprising a blank disposed between each lancet;

FIG. 16 is a perspective of the strip of lancets of FIG. 16 with a blank frangibly separated from the rest of the strip to expose a shroud about an exit and reentry slot for a lancet blade;

FIG. 17 is an inverted section along lines 17—17 of FIG. 15;

FIG. 18 is a segment of a section along lines 18—18 of FIG. 15;

FIG. 19 is a perspective of an unused single lancet comprising a lancet actuating arm prominently disposed on the outside of an outer lancet housing;

FIG. 20 is a perspective of the lancet seen in FIG. 19 after a completed lancing cycle;

FIG. 21 is a perspective of another unused single lancet housed in a self-contained transport package;

FIG. 22 is a perspective of the single lancet of FIG. 22, after the lancet has been used; and FIG. 23 is a cross section along lines 23—23 of FIG. 22, with some parts removed for clarity of presentation.

Figure 24:
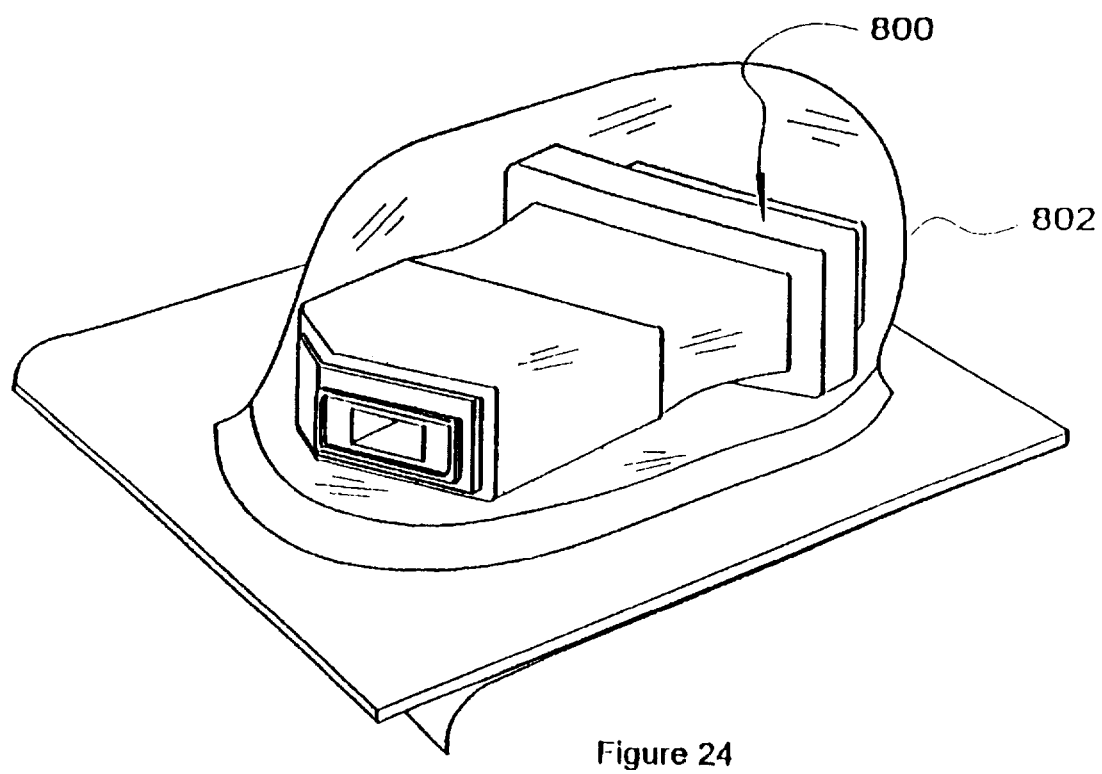
Figure 26:
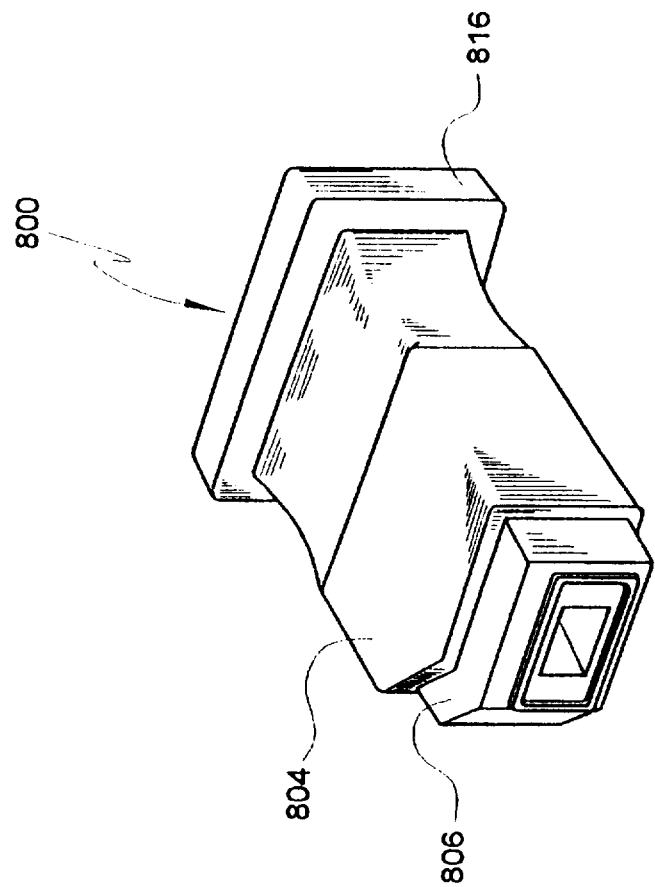
Figure 25:
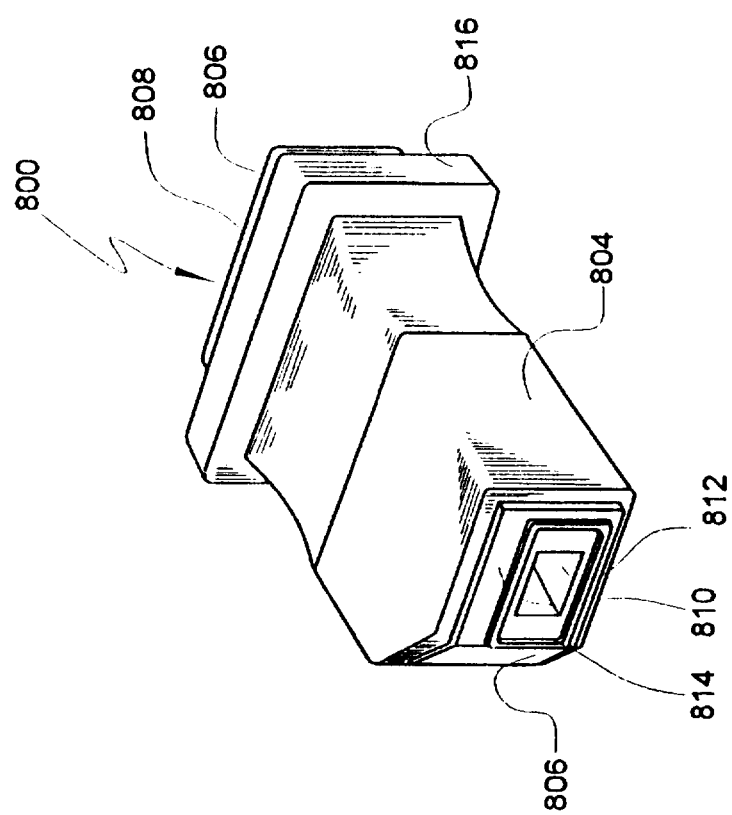

FIG. 24 is a perspective of an unused lancet disposed for protection in a bubble pack to retain lancet sterility;

FIG. 25 is a perspective of the unused lancet seen in FIG. 19, removed from the bubble pack for use;

FIG. 26 is a perspective of the lancet of FIG. 25, after use;

FIG. 27 is a top elevation of another single unused lancet with parts removed for clarity of presentation; and FIG. 28 is a top elevation of the lancet of FIG. 27, but after use.

DETAILED DESCRIPTION OF THE ILLUSTRATED EMBODIMENTS

In this description, the term proximal is used to indicate the segment of a device or other apparatus normally closer to a user when the device is properly used. The term distal refers to a direction which is farther removed from the user than a segment which is proximal. Reference is now made to the embodiments illustrated in FIGS. 1–28 wherein like numerals are used to designate like parts throughout. In order to properly reference novelty of the instant invention, a summary of a portion of the disclosure found in Smith is provided and referenced as prior art.

Reference is made to FIG. 1 which shows the inner surface of a lancet assembly member 10 of the preferred embodiment of Smith. Assembly member 10 comprises distal end 20, proximal end 30, and multiple empty housing compartments 40 separated by frangible segments 42 whereat the housing compartments can be easily manually separated without special tools. Assembly alignment pin holes 44 and 46 are also shown. Construction of each housing compartment 40, which is an integral operating portion of each individual lancet 41, is substantially the same as each of the others. As can be more easily seen in FIG. 2, typically each housing compartment 40 comprises a hub 50, a torsion spring anchor slot 62 which is an integral part of hub 50, a lancet blade slide plane 70, guides 80 and 81, and at least one frangible section 90, associated with frangible segment 42. Hub 50, placed substantially in the center of compartment 40, is part of the lancet triggering mechanism which is disclosed in detail hereafter. Groove 60 across the centerline of hub 50 provides a locking apparatus for that part of a torsion spring which will drive the lancet when the spring is freed to unwind. A torsion spring locking slot 62 holds a lower end of the torsion spring immobile in compartment 40. Lancet slide plane 70 is inset below an inner surface 92 to provide parallel lancet edge guides 80 and 81 which provide a controlled line of travel on each side of a lancet blade. The lancet slide plane 70, edge guides 80 and 81, and a travel limit edge 94 (described in detail hereafter), an integral part of the lancet structure and function, are included in the encapsulating housing structure in this embodiment.

A channel 96 which is an extension of slide plane 70 extends across a frangible area 42 such that, when a top cover completes the housing and separation occurs at frangible section 90, an egress/ingress port or aperture 98 is opened. The line of separation is determined by a "V" groove having an apex at section 90 and formed by compartment end apparatus comprising vertical end 102 and slanted end 104. Function of the frangible section and end apparatus is discussed in more detail later.

Other than a spring release associated with hub 50, moving parts of a total lancet assembly 100 (best seen in FIG. 2) comprise torsion spring 110 and lancet blade 120. A preferred embodiment of torsion spring 110 in Smith is shown in FIG. 2. Spring 110 comprises spring wire wound into a torsion spring having a lower end 122 which extends horizontally outward from a central core 123 of spring 110. On the other end, spring 110 is bent centrally such that it forms a straight horizontal segment 124 which can be locked into groove 60 when wound torsion spring 110 is press-fit over hub 50. To assemble a lancet according to Smith, a tightly wound torsion spring 110 is pressed over hub 50 such that lower spring end 122 is firmly affixed into anchor slot 62 and horizontal straight spring section 124 is firmly pressed into groove 60. At the wire end of straight segment 124 the spring is bent vertically upward forming crank arm 126 which is used to form an interlock between torsion spring 110 and a coupling slot 130 of lancet blade 120. Thus crank arm 126 comprises a cam and arcuate coupling slot 130 comprises a cam follower. The cam/cam follower structure, sometimes referred to as track structure, provides rotary to linear motion translation.

In Smith, lancet assembly 100 comprises lancet blade 120 which is of unitary, stainless steel construction comprising a very sharp lancet tip 140, torsion spring 110 coupling slot 130, guide edges 132 and 133, and leading edge 134. To complete assembly of lancet bottom housing 10 in a compartment 40, lancet blade slot 130 is placed over already positioned torsion spring crank arm 126 such that lance blade 120 lies on slide plane 70 with lancet tip 140 in channel 96 and edges 132 and 133 in line with edge guides 80 and 81.

Figure 4:
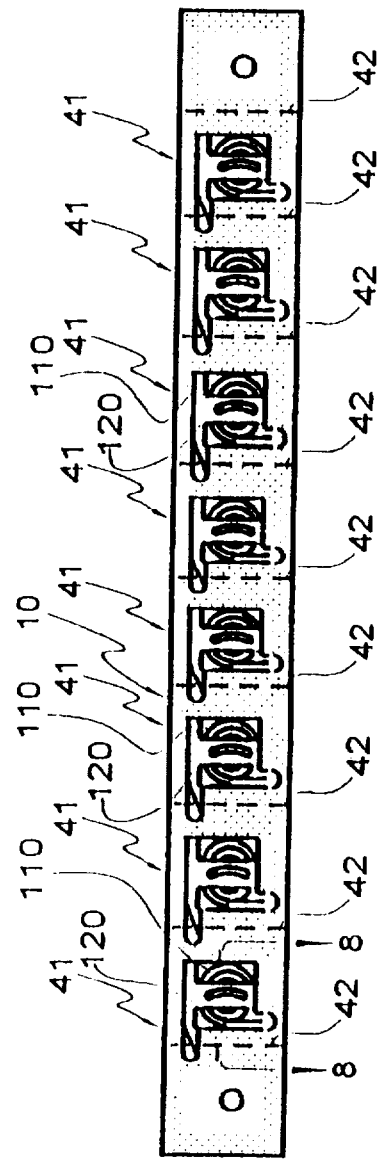
FIG. 4 is a planar view of the inner surface of the lancet housing assembly member seen in FIG. 1 with torsion spring and lancet blade in place and adhesive distributed on the higher surfaces.

A top elevation of lancet bottom housing 10 having a plurality of lancet blades 120 and springs 110 assembled therein is seen in FIG. 4. A housing cover, which normally covers lancet bottom housing 10 is not shown for clarity of presentation but is described in detail hereafter. Torsion spring 110 is cocked and held firmly in place by a slot 62 and a groove 60. Before lancet blade 120 can be fired, lancet tip 140 exit aperture 98 is opened by frangibly separating lancet bottom housing 10 within a frangible area 42.

The lancet is actuated by breaking attachment of hub 50 free from compartment 40. One mode of actuation is best seen in FIG. 9 which is a section along lines 9—9 of FIG. 4, with lancet blade 120 removed for clarity of presentation. Hub 50 is connected to compartment 40 by frangible diaphragm 142 comprising rounding annular corners 144 and sharp corners 146. Frangible diaphragm 142 comprises an annular actuator area 147 which first holds hub 50 from movement and, upon frangible actuation, releases hub 50 to rotate as forced by the released biasing memory of torsion spring 110. A recess 148 in diaphragm 142 causes actuator diaphragm 142 to be attached to hub 50 with a reduced cross section at sharp corners 146 forming actuator area 147. To actuate the lancet, an external force is applied to recessed portion 148 of diaphragm 142, causing actuator diaphragm 142 and hub 50 to be deflected slightly. Note that the recess 148 makes inadvertent deflection more unlikely. A deflection causes stresses to be generated at sharp corners 146 and results in fracture of hub 50 from actuator diaphragm 142 in the region of sharp corners 146. When viewed from inner surface 92. (see FIG. 2) freed hub 50 is released to spin in a counter clockwise direction as the biasing memory of the cocked torsion spring 110 is freed to unwind.

Figure 6:
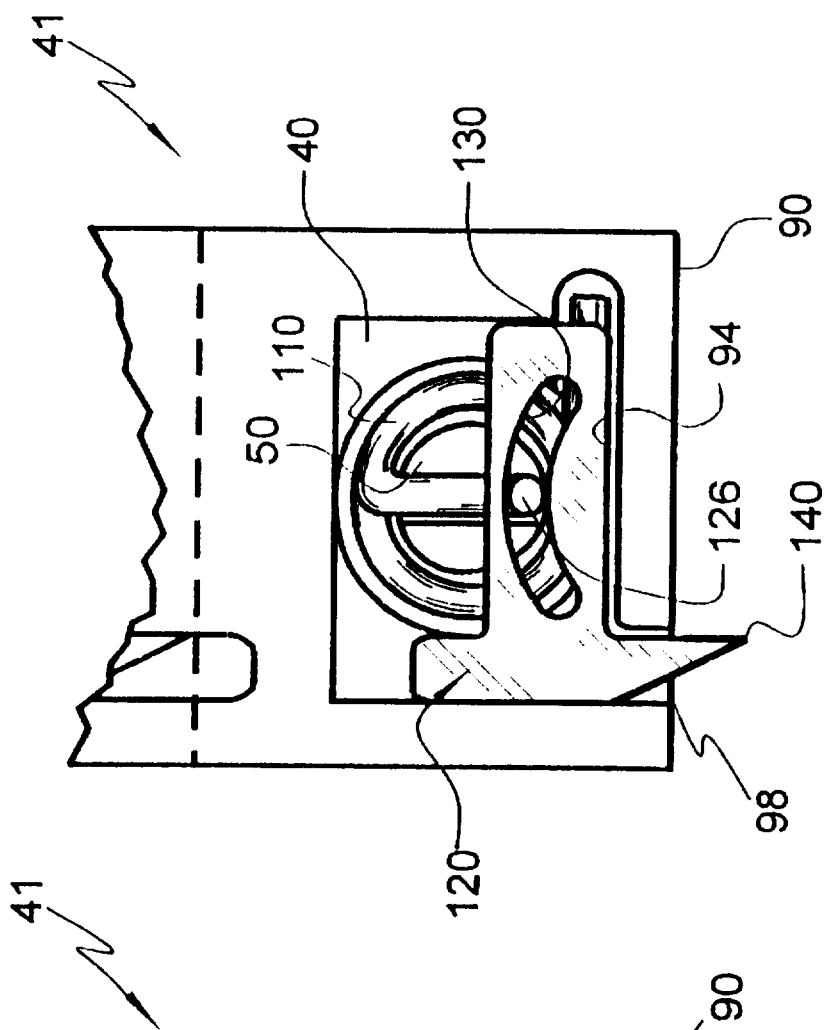
FIG. 6 is a top elevation of a lancet compartment depicted in FIG. 5 showing a fired lancet in mid-cycle wherein a tip of a lancet blade which is a key part of a lancet assembly is protruding from the lancet compartment.
Figure 5:
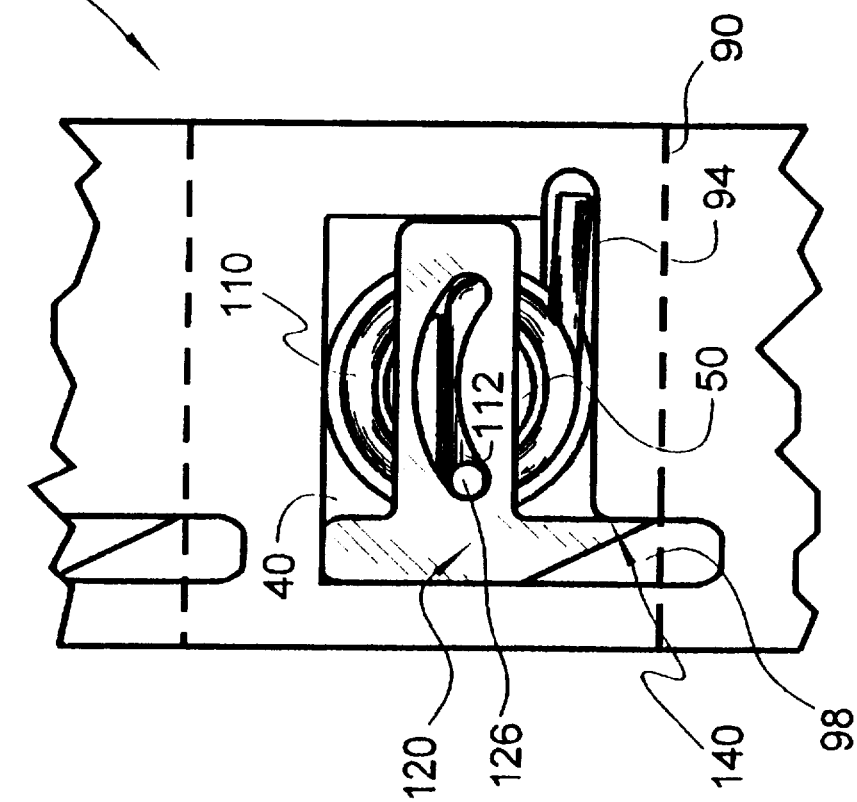
FIG. 5 is a top elevation of an assembled lancet housing assembly compartment seen in FIG. 1 without a cover.
Figure 7:
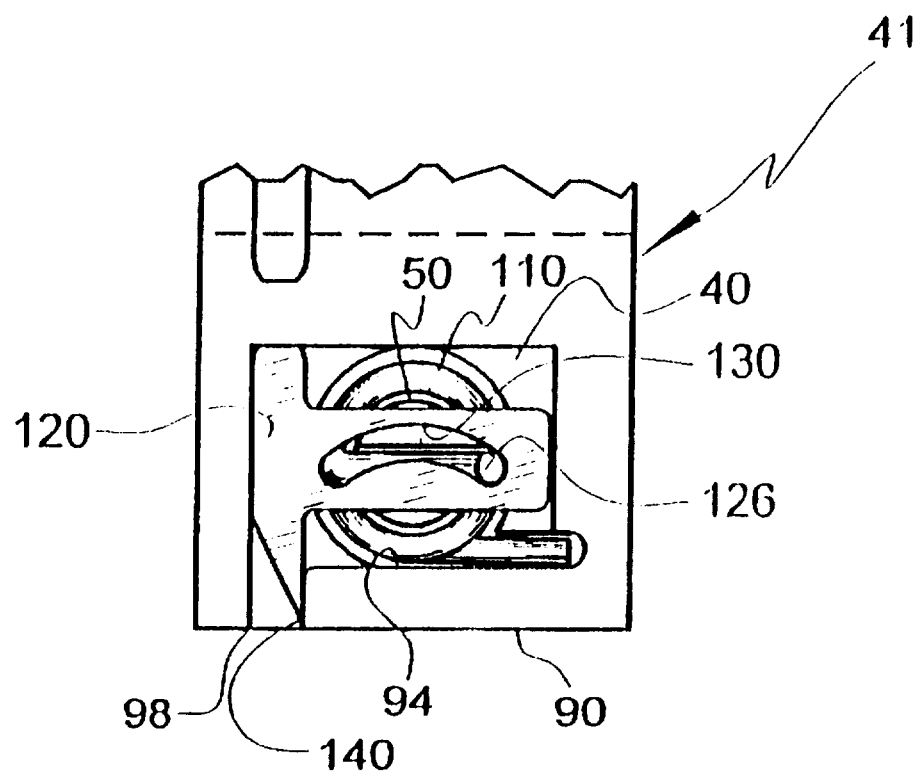
FIG. 7 is similar to FIG. 5, but showing a spent lancet with the lancet tip retracted into the lancet compartment.
Figure 8:
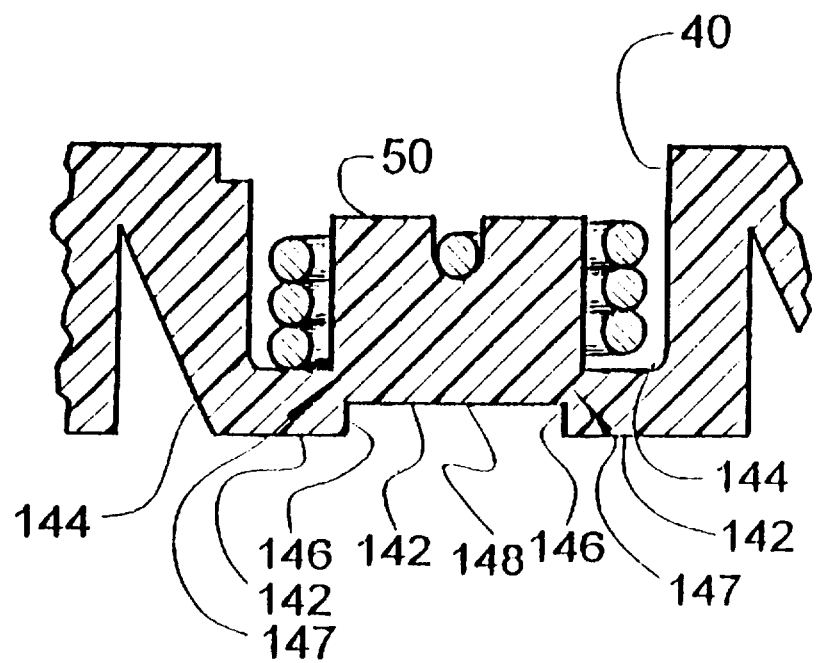
FIG. 8 is a section taken along lines 8—8 in FIG. 5; shown without a lancet blade for clarity of presentation.

As can best be seen in sequence in FIGS. 5, 6, and 7, as hub 50 and spring 110 rotate, crank arm 126 moves in an approximately circular motion, sliding laterally in slot 130 as it drives the lancet tip 140 linearly outward through the egress/ingress port 98 from the face of frangibly separated section 90. As shown in FIG. 6, lancet blade 120, guided by edges 80 and 81 and forced by crank arm 126, moves lancet tip 140 outward until crank arm 126 begin drawing blade 120 proximally back into cavity 40 which retards leading edge 134 of lancet blade 120 from colliding with travel limit edge 94. Leading edge 94 provides a safety limit for lancet blade tip 140 travel. In this manner, the depth of lancet tip 140 penetration is precisely determined. The depth of puncture in the currently preferred embodiment is 1.7 to 3.0 millimeters.

Further unwinding of torsion spring 110 continues to drive crank arm 126 in a nearly circular counter clockwise direction causing lancet blade 120 to be retracted as shown in FIG. 7, completing translation of torsion spring 10 rotary motion to bi-directional linear travel of lancet blade 120. With a cover in place, lancet compartment 40, now containing a totally retracted spent lancet 120, is a safe disposable. There is no "bounce" or multiple excursion of lancet tip 140 from the housing because the forcing direction of the biasing memory of the torsion spring forces lancet blade 120 away from travel limit edge 94 and egress/ingress port 98.

An enveloping or encapsulating housing cover 150 is shown in FIG. 3. Cover 150 is inverted, disposed to cover a bottom 10, after assembly, and permanently affixed thereto by either adhesion, ultrasonic bonding or another plastic adhesion method, such as thermal bonding. Once a spring 110 and a blade 120 are mounted into each lancet compartment 40, cover part 150 is accurately positioned relative to bottom 10 through the use of alignment pins and holes or by ridges and grooves used in ultrasonic bonding to cover every compartment 10. It is important that the strip formed by joining bottom 10 and cover 150 form a hermetically sealed unit which does not require further packaging for transport prior to use.

Smith discloses that both bottom 10 and cover 150 members may be molded from synthetic resinous material such as, but not limited to, polymethylmethacrylate, filled polypropylene, polystyrene, and acrylics. Depending upon material used, bonding may be accomplished by using methods comprising adhesives and thermal and ultrasound heating processes.

Either prior to or after encapsulation, all internal parts of the packets comprising a fully assembled lancet housing 200 (see FIG. 9) with precocked lancets can be sterilized by radiation or like methods which are well known in the art, making internally disposed finger piercing elements aseptic. Each lancet compartment is separately and hermetically sealed from all others such that contamination of the parts of one compartment does not contaminate parts of any other such that each encapsulated compartment 40 is its own hermetically sealed container, retaining an aseptic condition until egress/ingress port 98 is opened.

Reference is now made to FIGS. 9–12 wherein a lancet strip 200 and carrier 400 are seen. In use, carrier 400 holds lancet strip 200, comprising a joined bottom 10 and cover 150, for easier handling as strip 200 is serially shortened as each spent lancet housed in a compartment 40 is frangibly separated and discarded, as seen in FIGS. 10–12. Carrier 400 also provides a special tool for triggering each lancet. Except for blanks on proximal and distal ends 152 and 154, respectively, each individual lancet 41 is juxtaposed and so joined to an adjacent individual lancet 41, such that separating and discarding a lancet in a previously used individual lancet 41, generally results in exposing a lance blade exit orifice associated with a channel 96. If the newly exposed orifice is not used immediately, there is a significant likelihood a portion of the lancet travel channel 96 will become contaminated before ultimate use. As Smith teaches a slot which forms channel 96, there is a greater than desired likelihood that blood emitted from a lance site may contaminate an area surrounding the carrier 400 or carrier 400 itself. It is one of the main objects of this instant invention to correct for that event.

In the following detailed description of the instant invention, items which are similar in form and function to those of prior art described in Smith are commonly denoted by the same reference number primed. As an example, an individual lancet which is similar in form and function, but not entirely identical, to individual lancet 41 is denoted by 41' (see FIG. 15).

Attention is drawn to FIG. 13 wherein a lancet blade 500 of this instant invention is seen. Blade 500 is seen to comprise a slot 130', which is similar in form and function to slot 130, and a sharpened lancing tip 140'. However, blade 500 differs markedly from blade 120 by proximally disposed protrusions 502 and 504 on blade 500. As best seen in FIG. 13, blade 500 comprises an edge 506, transversely disposed to the direction of travel of lancet tip 140' and proximally disposed relative to slot 130'. On one side, edge 506 curves arcuately away from slot 130' at a rounded corner 508 to travel normal to the general direction of slot 130' and then curves inward and then outward to form a bulbus inwardly protruding section 510. Edge 506 then continues outward and forward (distal) to complete an outline of blade 500. On the other side, edge 506 curves similarly, but as a mirror image, arcuately away from slot 130' at a rounded corner 512 to also travel normal to the general direction of slot 130' and then curves inward and then outward to form a second bulbus inwardly protruding section 514. From this point edge 506 continues to define the entire circumference of blade 500.

The useful function of bulbus sections 510 and 514 is best seen in FIG. 14. As seen in FIG. 14, an I-beam section 515 having front and back plates 516 and 518 and separated by a pair of channels 520 and 522 which are proportioned to accept insertion of bulbus section 510 and 514, respectively, when vertically disposed provides nesting support for a plurality of blades 500. At the bottom of I-beam section 515, a feeder system which is of a form for feeding small, flat pieces is disposed to act as an automatic gravity feeder for an automatic assembly machine (not shown). Such feeders and automatic assembly machines are well known in the automated assembly equipment art. By trapping and nesting a plurality of blades in such an I-beam 515, blades are captured at a manufacturing site and transported and then individually fed for assembly into an individual lancet during an automatic assembly process. The presently preferred mode of manufacture of blades 500 is through a process of coining. A two step coining process produces a blade having virtually no rough edges and a sufficiently sharpened blade for lancing.

Attention is now directed to FIG. 15 wherein a strip 600 of individual lancets 41' generally interposed between blank parts 602 and 604 is seen. Strip 600 is comprised of a bottom part 10' and a cover part 150'. Parts 10' and 150' are similar in form and function to parts 10 and 150, but have marked and novel differences as disclosed hereafter. Each individual lancet 41' is frangibly separated from associated blank parts 602 and 604. It is preferred that blank part 604 be physically recognizable and separable from the other parts of strip 600 for ease of determining direction of entry into a carrier. (See, for example, FIG. 9.) Frange segments are denoted by segments alternately numbered 606 and 608 in FIGS. 15 and 16. Generally, franging at segment 606 separates a blank part 604 or 602 from an individual lancet 41' to expose a surface 610 of the individual lancet 41' for a lancing operation (as seen in FIG. 16).

It is important to note that the exposed surface 610 resulting from separating a blank (in FIG. 16 the blank is blank 604) further exposes a shroud 612 about a slot (not seen, but similar to the slot which forms channel 96, see FIGS. 5–7 and 11 and 12). Shroud 612 is formed by an arcuate raised section 614 in an inverted bottom 10' in combination with a planar raised section 616 in an attached cover 150'. Note that slopes on exposed face 620 formed in combination by parts of bottom 10' and cover 150' effectively extend shroud distally outward from the rest of strip 600 to aseptically isolate skin contacting areas of shroud 612. In this manner, blood and other material emitted from a lance site is either contained or effectively isolated from distal portions of a carrier or other portions of strip 600 to be used later. Note also that shroud 612 comprises a sterile interior face 622 when separated from a blank 604 or 602. Thus each subsequent individual lancet 41' presents a sterilely confined interface to its associated lance site.

Reference is now made to FIG. 17, wherein a bottom section 630 of an individual lancet 41' is seen. Section 630 comprises a hub 50', which is substantially the same as hub 50, earlier described, and which comprises a groove, numbered 60, as it is substantially the same in form and function to groove 60, earlier disclosed. Further, bottom section 630 comprises an actuator diaphragm 142', which, as is the case of actuator diaphragm 142, is frangibly broken under pressure normal to a surface (632), which is a portion of diaphragm 142'.

However, there is a major and critical difference between the structures of diaphragm 142 and hub 50 and of diaphragm 142' and hub 50'. Careful and detailed analysis of frange lines associated with parts molded in a form as disclosed for diaphragm 142 and hub 50 disclosed that franging hub 50 from diaphragm 142 would often result in creation of large fragments which would jut outward from hub 50 and catch and impede rotation of the hub and spring and therefore cause the lancet blade to misfire or not completely exit and return to compartment 40. Continued analysis showed that there appeared to be a characteristic flow path in molded parts which caused a somewhat surprising direction of development of a flow path and therefore a frange line. That path resulted in an annular frange path which was directed outward from a pressure placed upon a surface, such as surface 632. For this reason, an optimum frangible connection between a hub and an actuator diaphragm was determined to be through two annular grooves disposed about the base of the hub.

Relative dispositions of such grooves (annular grooves 634 and 636) are seen in FIG. 17. Two frange lines 638 and 640 are shown as examples of the effective area of franging where hub 50' separates from diaphragm 142'. Of course these are only examples, but it is important that grooves 634 and 636 be so positioned and of a depth that they intersect such an annular frange as hub 50' separates from diaphragm 142'. It is also important that grooves 634 and 636 be separated by sufficient material to permit physical stability until pressure is applied to surface 632. By experimentation, it has been shown that optimal pressure is in the range of 10 to 30 pounds and that, at the thinnest, material disposed between grooves 634 and 636 should be in the range of 0.010 inches (0.025 centimeters). Currently preferred material for bottom 630 and an associated cover is polystyrene, thirty percent filled with a mineral filler, such as wollastonite. In a currently preferred embodiment, bottom 630 is ultrasonically bonded to a cover. For this purpose, pointed protrusions 642 are molded into the upper segment of bottom 630. Otherwise, lancet cavity 40' is similar in form and function to cavity 40, previously described.

Seen in FIG. 18 is a longitudinal section of a portion of a bottom 630 comprising a first disposed blank 604 and a first-to-be-used individual lancet 41'. Note, dashed line 644, which denotes a frange line between blank 604 and individual lancet 41'. Franging along line 644 opens shroud 612, providing an exit and reentry portal for lancet blade 500, not seen in FIG. 18, for clarity of presentation. In FIG. 18, disposition of annular groove 634 relative to annular groove 636 is also seen. A next frange line 646 along which individual lancet 41' is broken away from the rest of other unused lancets is seen to be proximally disposed relative to dashed line 644.

Reference is now made to FIGS. 19 and 20 wherein a single lancet 700 (as opposed to a strip of lancets), is seen. Lancet 700 comprises an outer housing 702 and an inner housing 704. Outer housing 702 is a permanent part of lancet 700 and comprises a shroud portal 706 and an actuator button and lever 708. Further, outer housing comprises a box-like shape having a superior surface 710, an inferior surface 712, a portal side 714, a closed side 716 and a back side 718. Disposed for slidable insertion of inner housing 704 into outer housing 702, outer housing 702 comprises a fourth side 720 having an opening for slidable movement of inner housing 704.

Inner housing 704 comprises a cavity (not shown) which is referenced hereafter as cavity 41' due to its closeness in form and function with cavity 41', previously disclosed. However, rather than a direct and integral connection with a shroud, inner housing 704 comprises a substantially flat exit and entry portal 722 through which lancet blade tip 140' passes during a lancing cycle. Though not necessary, it is presently preferable that portal 722 have a slightly raised surface 724 by which inner housing 704 is frangibly affixed to a juxtaposed surface of outer housing 702 before use.

An unused lancet 700 is seen in FIG. 19. To prepare lancet 700 for use, inner housing 704 is translated laterally in the direction of arrow 725, perhaps by squeezing between a thumb and forefinger, until blade exit and reentry portal 722 is centrally disposed within shroud portal 706. Such a position is easily achieved as side 718 of outer housing 702 acts as a stop, limiting travel of housing 704. In the process of providing the force for laterally translating housing 704 relative to housing 702, any portion of housing 704 which is affixed to housing 702 is frangibly separated. Thus, prior to exerting the lateral translation force, the parts involved in frangibly affixing housing 702 to housing 704 are best used to serve as a sterile barrier about portal 722.

Once lancet 700 is prepared for use, shroud 706 is disposed about a site to be lanced and actuator button and lever 708 is depressed to frangibly separate a hub 50' from an actuator diaphragm 142', as disclosed earlier. Separation of hub 50' releases a spring 110 and thereby drives blade 500 and its associated blade tip 140' through a lancing cycle, leaving blade tip 140' safely confined in cavity 40' at the end of the cycle. It is evident that the step of preparation followed by a spring and blade actuation step inherently makes lancet 700 a two-step device.

Reference is now made to FIGS. 21–28 wherein parts and perspectives of one-step devices are seen. One step devices are defined to be lancets which are prepared for actuation and actuated in a single user movement. In FIGS. 21 and 22, a lancet 750 in an unused state (FIG. 21) and in a spent state (FIG. 22) is seen. Note that lancet 750 is similar in form to lancet 700. Lancet 750 comprises an outer housing 752 and an inner housing 754. The major difference, apparent from exterior views of lancets 700 and 750, is the lack of an actuator button and lever 708 on lancet 750.

Actuation of lancet 700 is caused by an internally disposed franging system which fires lancet 750 as inner housing 754 is transposed into outer housing 752. The mode of actuation of lancet 750 is clearly seen in FIG. 23. As seen in FIG. 23, inner housing 754 comprises a cavity 40', a spring 110, a blade 500, an actuator diaphragm 142" and a hub 50". The diaphragm 142" and hub 50" combination seen in FIG. 23 primarily differs from diaphragm and hub combinations disclosed previously above by an outwardly protruding conical hump 756 having a common axis with hub 50". Note that, in line with hump 756, outer housing comprises an open channel 758. Channel 758 is closed by an inwardly sloping surface 760. Sloping surface 760 is positioned to interact with hump 756 as inner housing 754 is translated into outer housing 752 at the time when portal 722 is approximately medially disposed within shroud portal 706. Inward movement of inner housing 754 ultimately causes surface 760 to collide with hump 756 placing increasing pressure upon diaphragm 142" until hub 50' is frangibly separated from the diaphragm. Note that the slope of surface 760 determines the mechanical advantage and therefore the rate of change of force which must be imposed upon inner housing 754 relative to outer housing 752 to actuate a lancing cycle. Currently preferred material for lancets 700 and 750 are the same as material specified for parts of strip 600.

Note that force to actuate lancet 750 is transverse to direction of travel of lancet tip 140'. Another embodiment of a one-step lancet, i.e. one-step lancet 800, is seen in FIGS. 24–26. There are two major differences between lancet 800 and lancet 750. The first difference is that lancet 750, like lancet 700, preferably comprises a frangible self-contained sterile seal disposed between a blade exit and reentry port (e.g. port 722) and an internal surface of a side of an outer housing (e.g. side 714). In this manner, no additional packaging is required to prevent contamination of a lancet blade before use. The second difference is direction of actuation. As earlier stated, actuation of lancet 750 is in a direction transverse to the motion of tip 140' during lancing while direction of applying force for actuating lancet 800 is parallel to the direction of movement of lancet tip 140'.

As actuation of lancet 800 and direction of travel of lancet tip 140' are disposed parallel one to the other, there is no opportunity of use a frangible part out of line of travel of lancet tip 140'. For this reason, prior to use, lancet 800 is preferably packaged inside a sealed package 802, an example of which is seen in FIG. 24. Such packages are well known in the medical industry and are commonly used to protect lancets in transport and prior to use.

Referring to FIG. 25, lancet 800 is seen to comprise an outer housing 804 and an inner housing 806. Inner housing 806 is made to slide within outer housing 804. Inner housing 806 comprises a plunger or push end 808 and an end 810. End 810 comprises a lancet tip 140' exit and reentry port 812 and a raised shroud 814. In combination, inner housing 806 and outer housing 804 comprise a lancet and lancet activation mechanism similar in form and function to that comprising hump 756 and sloped surface 760 except that the lancet activation mechanism is aligned to operate as outer housing 804 and inner housing 806 are moved one relative to the other, with outer housing 804 moving away from a lance site.

Outer housing 804 comprises a rim 816, which provides a housing 804 retarding part which permits outer housing 804 to be retracted from the lance site as plunger 808 is moved relative to outer housing toward the lance site to actuate lancet 800. The state of lancet 800 following a lancing procedure is seen in FIG. 26.

A lancet 900 comprising an additional mechanical advantage providing additional force to frange a hub 50" is seen in FIGS. 27 and 28. Similar to lancets 750, 800 and 850, lancet 900 comprises an outer housing 902 and an inner housing 904 which act as inner housing 904 is moved relative to outer housing 902 to actuate the lancet. The source of the mechanical advantage is a pivot pin 906 medially and proximally disposed relative to a lancet blade 500', disposed within inner housing 902.

Outer housing 902 further comprises a curved surface and associated part 908 which is juxtaposed to a lance site during a lancing procedure. Part 908 comprises a lancet tip exit and reentry portal 910 which also acts as a shroud. Outer housing 902 also comprises an opening 912 which permits a portion 914 of inner housing 904 to be slidably translated during activation of lancet 900.

Inner housing 904 comprises a lancet compartment 40" which is similar to cavity 40'. Inside compartment 40", inner housing 904 comprises a hub 50", a spring 110 and a lancet blade 500'. Lancet blade 500' comprises a medially disposed blade stem 915 and blade tip 140". Exterior to compartment 40", inner housing 904 comprises an aperture which is disposed about pivot pin 916 which provides a fulcrum and, in combination with the effective lever arm provided by portion 914 with mechanical advantage as portion 914 is translated inside outer housing 902 through opening 912. Inner housing 904 further comprises blade guides 918, 920, 922 and 924. Note that guide 924 is separated into two parts, making way for an anchor slot 62 for lower spring end 122. Inner housing 904 also comprises a curved surface 926 which is an arc of a circle drawn with pivot pin 906 at the center. Note that curvature of outer housing part 908 conforms with the curvature of surface 926. Curved surface 926 comprises an exit and reentry port 928 for lancet tip 140".

Before activation of lancet 900 by translating portion 914 into outer housing 902, an outer periphery 930 is preferably sealed against an inner surface portion of part 908 to permit lancet 900 to be transported and stored without additional packaging. In a manner similar to the frange mechanism provided by hump 756 and surface 760, outer housing 902 and inner housing 904 act in concert to frange hub 50" free to activate lancet 900 as inside housing 904 rotates about pivot pin 906 to bring port 928 in alignment with portal 910 and cause lancet tip 140" to traverse outward to the lance site and then return to a secure rest state as seen in FIG. 28.

Blade 500' differs from blade 500 in two significant ways. First tip 140" comprises a wider, but shallower cutting edge. Such a blade is useful in longer but more superficial cuts, such as cuts on an infant. Second stem 915 is medially disposed upon blade 500'. The medial position is particularly important in a device which rotates about a pivot pin as lancet 900 does.

It is currently preferred that materials used for lancets 700, 750, 800, and 900 are the same as those listed for lancet strip 600.

The invention my be embodied in other specific forms without departing from the spirit or essential characteristics thereof. The present embodiments are therefore to considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A one-time-use, disposable lancet actuating apparatus which is triggered to discharge a lancet tip from a lancet housing and to retract the lancet tip into the lancet housing for safe disposal, said apparatus comprising:

the lancet housing comprising at least one frangible part;

a lancet blade disposed within the lancet housing and comprising the lancet tip;

means for storing energy which is also disposed within the lancet housing and which is adapted to be selectively released from a state of high potential energy to provide a unidirectional angular form of kinetic energy, said energy storing means comprising means for driving said blade linearly outward from and inward into said lancet housing as a result of said angular form of kinetic energy and for communicating with a catch which further communicates with a triggerable release;

said lancet housing further comprising a hub which in an initial state is an integral and is a frangibly releasible part of said lancet housing, said hub comprising a frangibly releasing section the catch and a base which communicates through said frangibly releasing section to the rest of said lancet housing as a part of said triggerable release and which communicates through the hub to the catch for said communicating means; and said frangibly releasing section comprising a pair of concentric grooves, at least one of said grooves circumscribing said base, said grooves in combination defining a region, interposed between said grooves, in which substantially all segments of said lancet housing which frange when the base of the hub is placed under stress and separated from the rest of the lancet housing are disposed.

2. A one-time-use, disposable lancet actuating apparatus according to claim 1, wherein said lancet housing comprises an orifice through which the lancet tips travels outwardly and inwardly.

3. A one-time-use, disposable lancet actuating apparatus according to claim 2, wherein said lancet housing further comprises a shroud disposed about said orifice, said shroud comprising a raised surface which acts to contain flow of fluid resulting from action of the lancet.

4. A one-time-use, disposable lancet actuating apparatus according to claim 1, wherein said lancet housing comprises a linear strip comprising a plurality of frangibly connected lancet devices.

5. A one-time-use, disposable lancet actuating apparatus according to claim 1, wherein said lancet housing comprises only a single lancet device.

6. A one-time-use, disposable lancet actuating apparatus according to claim 1, wherein said apparatus comprises two housing parts, said lancet housing and a second housing, said lancet housing disposed as an inner housing slidably disposed inside said second housing, said lancet and second housings being moved one relative to the other to form said triggerable release for frangibly separating the hub from the lancet housing.

7. A one-time-use, disposable lancet actuating apparatus according to claim 6, wherein said lancet and second housings, in combination, comprise means for moving said lancet housing relative to said second housing in a direction which is transverse to direction of linear movement of said lancet tip.

8. A one-time-use, disposable lancet actuating apparatus according to claim 6, wherein said lancet and second housings, in combination, comprise means for moving said lancet housing relative to said second housing in a line of movement substantially parallel to direction of linear movement of said lancet tip.

9. A one-time-use, disposable lancet actuating apparatus which is triggered to discharge a lancet tip from a lancet housing and retract the lancet tip into the lancet housing for safe disposal, said apparatus comprising:

at least one lancet housing frangibly joined to a blank, said blank comprising a closure over a portion of said lancet housing which comprises an orifice through which said lancet tip is discharged and retracted, said orifice being opened when the blank is removed from the lancet housing prior to, and in preparation for, use of the apparatus in a medical procedure; the lancet housing comprising a top part securely affixed to a bottom part;

a lancet blade disposed within the lancet housing and comprising the lancet tip;

means for storing energy which is selectively released from a state of high potential energy to provide a unidirectional angular form of kinetic energy, said energy storing means comprising means for driving said blade linearly outward from and inward into said lancet housing as a result of said angular form of kinetic energy and for communicating with a catch which further communicates with a triggerable release;

inwardly and a shroud disposed as an interface between said lancet housing and said blank, said shroud being disposed about said orifice after the blanks removed and comprising an arcuately a raised surface disposed in said bottom part and a complementary raised surface disposed in said top part which in combination act to contain flow of fluid resulting from action of the lancet.

10. A one-time-use, disposable lancet actuating apparatus according to claim 9 wherein each of said raised surface comprises an edge which is affixed to a frangible portion of said housing and, when displaced from the frangible portion comprises an internal surface which is not contaminated by material externally disposed to said housing before displacing the frangible portion.

11. A one-time-use, disposable lancet actuating apparatus according to claim 9 wherein said lancet housing comprises a linear strip comprising a plurality of frangibly connected lancet housings and associated blanks.

12. A one-time-use, disposable lancet actuating apparatus according to claim 9 wherein said lancet housing comprises only a single lancet device.

13. A one-time-use, disposable lancet actuating apparatus according to claim 9 wherein said apparatus comprises two housing parts, said lancet housing and a second housing, said lancet housing disposed as an inner housing slidably disposed inside said second housing, said lancet and second housings being moved one relative to the other to form said triggerable release for frangibly separating a hub part from the rest of the lancet housing.

14. A one-time-use, disposable lancet actuating apparatus according to claim 13 wherein said lancet and second housings, in combination, comprise means for moving said lancet housing relative to said second housing in a direction which is transverse to direction of linear movement of said lancet tip.

15. A one-time-use, disposable lancet actuating apparatus according to claim 13 wherein said lancet and second housings, in combination, comprise means for moving said lancet housing relative to said second housing in a line of movement substantially parallel to direction of linear movement of said lancet tip.

* * * * *